United States Patent
Kohout

(10) Patent No.: US 6,393,843 B2
(45) Date of Patent: May 28, 2002

(54) EXTENDED LIFE THERMAL PACK

(75) Inventor: Daniel J. Kohout, Grayslake, IL (US)

(73) Assignee: Allegiance Corporation, McGaw Park, IL (US)

( * ) Notice: Subject to any disclaimer, the term of this patent is extended or adjusted under 35 U.S.C. 154(b) by 0 days.

(21) Appl. No.: 09/769,218

(22) Filed: Jan. 24, 2001

Related U.S. Application Data

(63) Continuation-in-part of application No. 09/263,056, filed on Mar. 6, 1999, now Pat. No. 6,233,945.

(51) Int. Cl.$^7$ ................................. F25D 5/00; F24J 3/00
(52) U.S. Cl. ........................... 62/4; 252/70; 126/263.08
(58) Field of Search .............. 62/4; 252/70; 126/263.01, 126/263.08, 263.09

(56) References Cited

U.S. PATENT DOCUMENTS

| | | | | |
|---|---|---|---|---|
| 2,573,791 A | * | 11/1951 | Howells | 128/82.1 |
| 3,095,291 A | | 6/1963 | Robbins | 62/4 |
| 3,149,943 A | | 9/1964 | Amador | 62/4 |
| 3,175,558 A | | 3/1965 | Caillouette et al. | 128/403 |
| 3,643,665 A | | 2/1972 | Caillouette | 128/403 |
| 3,736,769 A | | 6/1973 | Petersen | 62/530 |
| 3,763,622 A | | 10/1973 | Stanley, Jr. | 53/25 |
| 3,804,077 A | | 4/1974 | Williams | 126/263 |
| 3,892,060 A | | 7/1975 | Stanley, Jr. | 53/127 |
| 3,950,158 A | | 4/1976 | Gossett | 62/4 |
| 3,957,472 A | | 5/1976 | Donnelly | 62/4 |
| 3,977,202 A | | 8/1976 | Forusz et al. | 62/4 |
| 4,049,408 A | | 9/1977 | Patel | 62/4 |
| 4,081,256 A | | 3/1978 | Donnelly | 62/4 |
| 4,397,315 A | | 8/1983 | Patel | 128/403 |
| 4,462,224 A | | 7/1984 | Dunshee et al. | 62/530 |
| 4,596,250 A | | 6/1986 | Beisang, III et al. | 128/402 |
| 4,750,493 A | | 6/1988 | Brader | 128/380 |
| 4,780,117 A | | 10/1988 | Lahey et al. | 62/4 |
| 4,856,651 A | | 8/1989 | Francis, Jr. | 206/219 |
| 4,953,550 A | | 9/1990 | Dunshee | 128/403 |
| 4,967,573 A | | 11/1990 | Wilhelm | 62/530 |
| 4,993,237 A | | 2/1991 | Bond et al. | 62/294 |
| 4,995,217 A | | 2/1991 | Francis, Jr. | 53/410 |
| 5,178,139 A | | 1/1993 | Angelillo et al. | 128/403 |
| 5,184,613 A | | 2/1993 | Mintz | 128/402 |
| 5,211,949 A | | 5/1993 | Salyer | 424/402 |
| 5,261,241 A | | 11/1993 | Kitahara et al. | 62/4 |
| 5,274,865 A | | 1/1994 | Takehashi | 5/644 |
| 5,277,180 A | | 1/1994 | Angelillo et al. | 607/114 |
| 5,314,005 A | | 5/1994 | Dobry | 165/10 |
| 5,393,462 A | | 2/1995 | Avery | 252/315.5 |
| 5,409,500 A | | 4/1995 | Dyrek | 607/111 |
| 5,417,276 A | | 5/1995 | Dobry | 165/10 |
| 5,417,721 A | | 5/1995 | Mallasch | 607/108 |
| 5,431,022 A | | 7/1995 | Abe | 62/4 |
| 5,486,206 A | | 1/1996 | Avery | 607/104 |
| 5,552,075 A | | 9/1996 | Salyer | 252/70 |
| 5,603,729 A | | 2/1997 | Brown et al. | 607/114 |
| 5,650,090 A | | 7/1997 | Salyer | 252/70 |
| 6,233,945 B1 | * | 5/2001 | Kohout | 62/4 |

* cited by examiner

Primary Examiner—William C. Doerrler
(74) Attorney, Agent, or Firm—Andrew G. Rozycki

(57) ABSTRACT

The invention relates to extended life thermal packs. In one embodiment, the thermal pack comprises a container having a first thermally reactive chemical solute therein, a rupturable solvent packet containing a solvent, and a rupturable solute packet containing a second thermally reactive chemical solute in the solute packet. The solutes are chemically separated until time of use and are different from one another. The chemical separation of solutes until time of use in combination with the structure of the thermal pack structure afford both extended duration of thermal effect by the pack and afford the user with increased control by permitting optional sequential combination of the reactants. The thermal reaction produced by the combination of solute and solvent can be either endothermic or exothermic and therefore can be used to apply cold or hot therapy, respectively.

62 Claims, 5 Drawing Sheets

EXTENDED LIFE THERMAL PACK

RELATED APPLICATION DATA

This application is a continuation-in-part of U.S. patent application Ser. No. 09/263,056 filed Mar. 6, 1999, now U.S. Pat. No. 6,233,945 B1 issued May 22, 2001.

FIELD OF THE INVENTION

The invention disclosed herein relates to the field of thermal packs. In particular, the invention relates to thermal packs wherein reduced or elevated temperatures can be generated for extended periods of time.

BACKGROUND OF THE INVENTION

The use of thermally reactive chemical systems in thermal packs is known. Typical uses of hot and cold packs include thermal therapy for treatment of muscle soreness, injuries such as sprains, maintenance of food and beverage temperature, and the like. The treatment of injuries or sore muscles using a hot pack is generally referred to as "warm therapy" or "heat therapy", and the treatment using a cold pack is generally referred to as "cold therapy". In the case of cold therapy, because the swelling associated with the injury or sore muscle begins almost immediately with the onset of injury, or the stress inducing the soreness, treatment should begin promptly. Conditions which benefit from heat therapy include hypothermia and thermal shock. Accordingly, it is desirable that whatever the source of thermal therapy used for such treatment, the thermal therapy source should be readily available, easy to use, and capable of providing thermal therapy for a duration that is effective in treating the injury, sore muscle or condition.

Several general types of thermal packs are known in the art. There are cold packs that contain an insulating material which, upon cooling in a refrigerator or freezer, gradually warm back to ambient temperature. Likewise, there are hot packs which contain an insulating material and are heated to a temperature which gradually cool to ambient temperature. There are hot and cold packs that operate via phase change of the thermal pack components. Also, there are thermal packs that employ chemical components that dissolve endothermically or exothermically in a solvent.

Examples of cold packs that employ an insulating material include cold packs that contain gelling agents, such as the thermal packs described in Williams U.S. Pat. No. 3,804,077 and Dunshee et al. U.S. Pat. No. 4,462,224. For example, these cold packs are cooled in a refrigerator or freezer. Once cooled, the cold pack is placed on the injured or sore area and thus provides cold therapy. Typical gels used in this type of cold pack are based on the gelation of xanthan gum, locust bean gum, gum tragacanth, guar gum, hydroxypropyl methylcellulose, absorbent poylmers, and the like. Gels may also be based on a high molecular weight polyacrylic acid cross-linked with a polyalkenyl ether, also referred to as cis-carbomers.

Other examples of cold packs that employ an insulating material exist in the art. For example, cold packs may employ an outer insulative layer. Alternatively, clays or silicates can be used in conjunction with cold therapy providing chemicals to form aqueous colloidal dispersions sometimes referred to as gels. These colloidal dispersions perform a similar life-extending function due to steric hindrance provision during dissolution.

Phase change materials can be converted between solid and liquid phases and utilize their latent heat of fusion to cool or heat during such phase conversion. The latent heats of fusion are greater than the sensible heat capacities of the materials. Accordingly, the amount of energy absorbed upon melting or released upon freezing is greater than the amount of energy absorbed or released upon increasing or decreasing the temperature of the material by 10° C. within a phase. Water or the silica based materials described in Salyer U.S. Pat. No. 5,211,949 are examples of phase change materials.

Certain chemical compounds, once dissolved into a solution, result in a lowering of the temperature of the solution below ambient temperature. On dissolution, these compounds take up heat from the surrounding environment. For example, inorganic salts or soluble organic compounds known to have a positive (greater than zero) enthalpy ($\Delta_{sol} H°$) of aqueous solution are used to make the reduced temperature solutions useful in cold packs. However, solvents other than water can be used so long as $\Delta_{sol} H°$ of the solute is greater than zero. Similarly, there are also chemical compounds which upon dissolving in solution result in elevated temperatures above ambient temperature including inorganic salts or soluble organic compounds known to have a negative (less than zero) enthalpy ($\Delta_{sol} H°$) of aqueous solution. These compounds are used to make elevated temperature solutions useful in hot packs. Other ingredients can be added to these compounds as well. For example, alternative solvents can be used in hot packs.

Any of these types of thermal packs can be used in combination with one another. For example, cold packs which employ a gel can also contain endotherm-producing compounds. Phase change materials can also be used in combination with endotherm-producing compounds or exotherm-producing compounds.

One problem associated with conventional thermal packs is the short duration of the temperature effect. To be useful in thermal therapy, the thermal pack must provide the desired temperature effect for a period of time needed for the particular therapy or use.

Thermal packs of the type that employ thermally reactive chemicals have employed various methods to extend the cold duration or the "life" of the thermal pack. Methods of extending the life of thermal packs can be summarized into three categories: 1) physical means to slow dissolution of the endotherm-producing or exotherm-producing chemical; 2) temperature means to provide a large temperature differential with respect to an ambient temperature; and 3) insulation means to control the rate of heat absorption or retention in an attempt to increase the time the thermal pack is at a desired temperature.

Physical means to slow dissolution of the endotherm-producing and exotherm-producing chemicals can use coated solutes whereby the coating slows dissolution. Thermal packs of this type have also used endotherm-producing or exotherm-producing chemicals pressed into pellets. For example, coated particles which control the reaction rate in cool packs are described in Lahey et al. U.S. Pat. No. 4,780,117. The pellet-form slows the dissolution of the endotherm-producing chemical and thus prolongs the life of the cold pack.

The second category wherein temperature means is used to provide a large temperature differential with respect to an ambient temperature operates by increasing temperature differential and thereby increasing the time required for the cold pack to return to ambient temperature. For example, the large temperature differential can be accomplished by using one or two endotherm-producing chemicals whereby one of the chemicals reduces temperature to an extremely low value and the other reduces the temperature to one which is useful for cold therapy. Similarly, two exotherm-producing chemicals, or a combination of one exothermic and one endothermic chemical, have been used to maintain usable temperature ranges.

Thermal packs which employ gelling agents are included in the third category of methods for extending the life of cold and hot packs. The gelling agents can be included in the same container as the endotherm-producing or exotherm-producing chemical. One example of a typical gelling agent is hydroxypropylmethylcellulose. When initiated, the endotherm-producing chemical reduces the temperature of the cold pack and the gelling agent gels. The formed gel provides some level of dissolution hindrance so the rate of dissolution is decreased.

Thermal device structures have also been explored as a means to extend the life of thermal packs. One such device is described in Brown et al., U.S. Pat. No. 5,603,729, wherein a prolonged reaction thermal device having three compartments and thermally reactive ingredients is described. A solvent is separated from two water-dissolving containers each containing ammonium nitrate and having varying thickness to control the rate of dissolution. The extended life, however, is the result of the rate of dissolving of the solute-containing pouches.

Each of the above thermal packs and methods of extending life thereof have proven to be unreliable, uncontrolled, or cumbersome. Many conventional cold packs and hot packs produce a useful temperature for a relatively short duration. Therefore, the thermal pack may be ineffective in providing adequate thermal therapy or maintenance of food or beverages at appropriate temperature levels. Attempts to extend the reduced temperature duration have presented problems. If the means to extend the life of the thermal pack is based on using a large initial temperature differential, the pack will most likely generate an unsuitable temperature for its intended use. This is especially important in therapeutic applications of the thermal packs.

It is generally understood that a thermal pack will maintain a temperature for increasing amounts of time as the concentration of thermal chemical increases. It is also generally understood that many endotherm-producing and exotherm-producing chemicals are salts. Generally, thermal packs which employ endothermic or exothermic salts are used only one at a time, and once the pack has attained a temperature at which it is no longer useful, it is thrown away. Certain disposal regulations, however, limit the amount of these endotherm-producing and exotherm-producing salts used in thermal packs. The concentration of these salts, therefore, cannot be increased without limit.

What would be advantageous, therefore would be a thermal pack having an extended life which does not require the use of potentially costly insulting means. Even more advantageous would be a thermal pack which provides extended life at a usable or suitable temperature and which employs salt concentrations that comply with regulatory requirements. Furthermore, a thermal pack wherein the extended life is the combined result of both chemical factors as well as the user's ability to control the timing of the thermal reaction or sequential thermal reactions would be particularly useful.

SUMMARY OF THE INVENTION

The invention provides for a thermal pack (i.e., hot or cold pack) with an extended life wherein the desired temperature for its intended application is maintained. In other words, the thermal pack of the invention employs a temperature differential with respect to ambient temperature appropriate for its intended application initially and through the duration of its use. Furthermore, the method for extending life of the thermal pack of the invention is independent of particle size or coatings, or additional insulation techniques. Instead, the thermal packs of the invention not only afford extended life by controlling the saturation of the solvent, but also provide the user with the ability to control the initiation of sequential thermal reactions as well and thus "regenerating" the pack in accordance with the user's particular preferences or needs.

The invention provides a thermal pack comprising a solvent and at least two solutes (first and second endotherm-producing chemicals in the case of a cold pack or first and second exotherm-producing chemicals in the case of hot packs), wherein the solutes are chemically separated until time of use. Thermal packs according to the invention comprise at least three compartments which chemically separate the solvent and each of the solutes from one another. The extended life, or duration of thermal effect, of a thermal pack in accordance with the invention is afforded by the chemical reaction between the solvent and the simultaneous or sequential combination of the two different solutes alone separated from one another until time of use, in conjunction with the structure of the thermal pack components. In other words, thermal pack structural features can be used to control the temperature and duration of the thermal effect in addition to the chemical aspects of the thermal pack, i.e., selection of the thermally reactive chemicals to control the useful temperature and extend the life of the thermal pack. Furthermore, the chemical separation of the solutes from one another until time of use prevents undesired chemical reactions between the solutes which can occur as a result of chemical incompatibility and storage conditions.

The invention provides for a thermal pack adapted to extend the duration of thermal effect comprising: a container sealed to the atmosphere; a first thermally reactive chemical solute disposed within said container; a rupturable solvent packet disposed within said container; a solvent disposed within said solvent packet; a rupturable solute packet disposed within said container; a second thermally reactive chemical solute disposed within said solute packet; wherein each of the solvent, and each of the first and second thermally reactive solutes are chemically separated and wherein the first thermally reactive solute is different from the second thermally reactive solute.

Another embodiment of the invention provides for a thermal pack adapted to extend the duration of thermal effect comprising: a container sealed to the atmosphere; a first thermally reactive chemical solute disposed within said container; a rupturable solvent packet disposed within said container; a solvent disposed within said solvent packet; a first rupturable solute packet disposed within said container; a second thermally reactive chemical solute disposed within said first rupturable solute packet; a second rupturable solute packet disposed within said container; a third thermally reactive chemical solute disposed within said second rupturable solute packet; wherein each of the solvent, first, second and third thermally reactive solutes are chemically separated and wherein at least two of the first, second and third thermally reactive solutes are different from each other.

In yet a further embodiment, the invention provides for a thermal pack adapted to extend the duration of thermal effect comprising: a container sealed to the atmosphere; a first thermally reactive chemical solute disposed within said container; a first rupturable solvent packet disposed within said container; a first solvent disposed within said first solvent packet; a second rupturable solvent packet disposed within said container; a second solvent disposed within said second solvent packet; a first rupturable solute packet disposed within said container; a second thermally reactive chemical solute disposed within said first solute packet; a second rupturable solute packet disposed within said container; a third chemically reactive solute disposed within said second rupturable solute packet; wherein each of the first and second solvents, first, second and third thermally reactive solutes are chemically separated, and wherein at least two of the first, second and third thermally reactive solutes are different from each other.

In yet another embodiment, the invention provides for a thermal pack adapted to extend the duration of thermal effect having first and second containers each sealed to the atmosphere and from the other, each of said first and second containers comprising: a first thermally reactive solute disposed within said container; a rupturable solvent packet disposed within the container; a solvent disposed within said solvent packet; a rupturable chemical solute packet disposed within said container; a second thermally reactive solute disposed within said rupturable solute packet; wherein each of the solvent, first and second thermally reactive solutes are chemically separated until use and wherein the first thermally reactive solute is different from the second thermally reactive solute.

In each of the above embodiments, a cold pack contains endotherm-producing solutes when reacted with the solvent or solvents. Likewise, a hot pack contains exotherm-producing solutes when reacted with the solvent or solvents.

Another aspect of the invention provides a method of applying thermal treatment to a body comprising: a) selecting a thermal pack adapted to extend the duration of thermal effect comprising a container sealed to the atmosphere, a first thermally reactive chemical solute disposed within said container, a rupturable solvent packet disposed within said container, a solvent disposed within said solvent packet, a rupturable solute packet disposed within said container, a second thermally reactive chemical solute disposed within said solute packet, wherein each of the solvent, the first and second thermally reactive solutes are chemically separated and wherein the first thermally reactive solute is different from the second thermally reactive solute; b) rupturing solvent packet so as to combine with first solute; c) rupturing the solute packet thereby combining the second solute with the solvent; and d) applying the thermal pack to the body.

The invention further provides for a method of applying thermal treatment to a body comprising: a) selecting a thermal pack adapted to extend the duration of thermal effect comprising a container sealed to the atmosphere, a first thermally reactive chemical solute disposed within said container, a rupturable solvent packet disposed within the container, a solvent disposed within the solvent packet, a first rupturable solute packet disposed within the container, a second thermally reactive chemical solute disposed within the first solute packet, a second rupturable solute packet, a third thermally reactive chemical solute disposed within the second rupturable solute packet, wherein each of the solvent, first second and third thermally reactive solutes are chemically separated and wherein at least two of the first second and third thermally reactive solutes are different from each other; b) rupturing solvent packet so as to combine said solvent with said first solute; c) rupturing the first solute packet thereby combining the second solute with the solvent; d) rupturing the second solute packet thereby combining the third solute with the solvent; and e) applying the thermal pack to the body.

The invention also provides for a method of applying thermal treatment to a body comprising: a) selecting a thermal pack adapted to extend the duration of thermal effect comprising a container sealed to the atmosphere, a first thermally reactive chemical solute disposed within the container, a first rupturable solvent packet disposed within the container, a first solvent disposed within the rupturable solvent packet, a second rupturable solvent packet disposed within the container, a second solvent disposed within the second rupturable solvent packet, a first rupturable solute packet disposed within the container, a second thermally reactive chemical solute disposed within the first rupturable solute packet, container, second rupturable solute packet disposed within the container, a third thermally reactive chemical solute disposed within the second rupturable solute packet, wherein each of the first and second solvents, first second and third thermally reactive solutes are chemically separated, and wherein at least two of the first, second and third thermally reactive solutes are different from each other; b) rupturing the first solvent packet so as to combine said solvent with said first thermally reactive solute; c) rupturing the first solute packet thereby combining the second thermally reactive solute with the first solvent; d) rupturing the second solvent packet thereby combining the second solvent with the first and second solutes; e) rupturing the second solute packet thereby combining the third solute with the first and second solvent; and f) applying the thermal pack to the body.

Yet another aspect of the invention provides for a method of applying thermal treatment to a body comprising a) selecting a thermal pack adapted to extend the duration of thermal effect comprising first and second containers each sealed to the atmosphere and from the other, each of said first and second containers comprising a first thermally reactive chemical solute disposed within said container, a rupturable solvent packet disposed within said container, a solvent disposed within said solvent packet, a rupturable solute packet disposed within said container, a second thermally reactive chemical solute disposed within said rupturable solute packet, wherein each of the solvent, first and second thermally reactive solutes are chemically separated and wherein the first thermally reactive solute is different from the second thermally reactive solute; b) rupturing solvent packet in the first container so as to combine said first solvent with said first solute; c) rupturing the solute packet in the first container thereby combining the second solute with said solvent; d) applying the thermal pack to the body; e) rupturing the solvent packet in the second container so as to combine said solvent with said first solute; f) rupturing the solute packet in the second container thereby combining the second solute with the solvent; and g) reapplying the thermal pack to the body.

It will be understood that the step of applying the thermal pack to the body can occur at any point after the initiation of the thermal reaction resulting from the combination of the solvent with the solute(s), irrespective of the various possible rupturing sequences. The thermal treatment can be in the form of either cold or heat therapy.

DETAILED DESCRIPTION OF THE INVENTION

As used herein, the term "therapeutically useful" as used in the context of temperatures produced by the thermal packs of the invention, is meant to include temperatures appropriate for the intended use or application.

The term "thermal" as used herein within the context of describing the packs of the invention or resulting temperatures of the reactive chemicals is intended to encompass either hot or cold effect. Likewise, the term "thermally reactive" is meant to refer to a chemical reaction which reduces temperatures (i.e., endothermic) or elevates temperatures (i.e., exothermic).

The term "chemically separated" is meant to indicate separation by a barrier which is airtight and liquid impermeable such that no chemical interaction between substances on opposing sides of the barrier can occur. In the context of the packet materials and container as the barriers, the term refers to the structural separation of the solvent and solute components and absence of contact between them.

Figure 1:
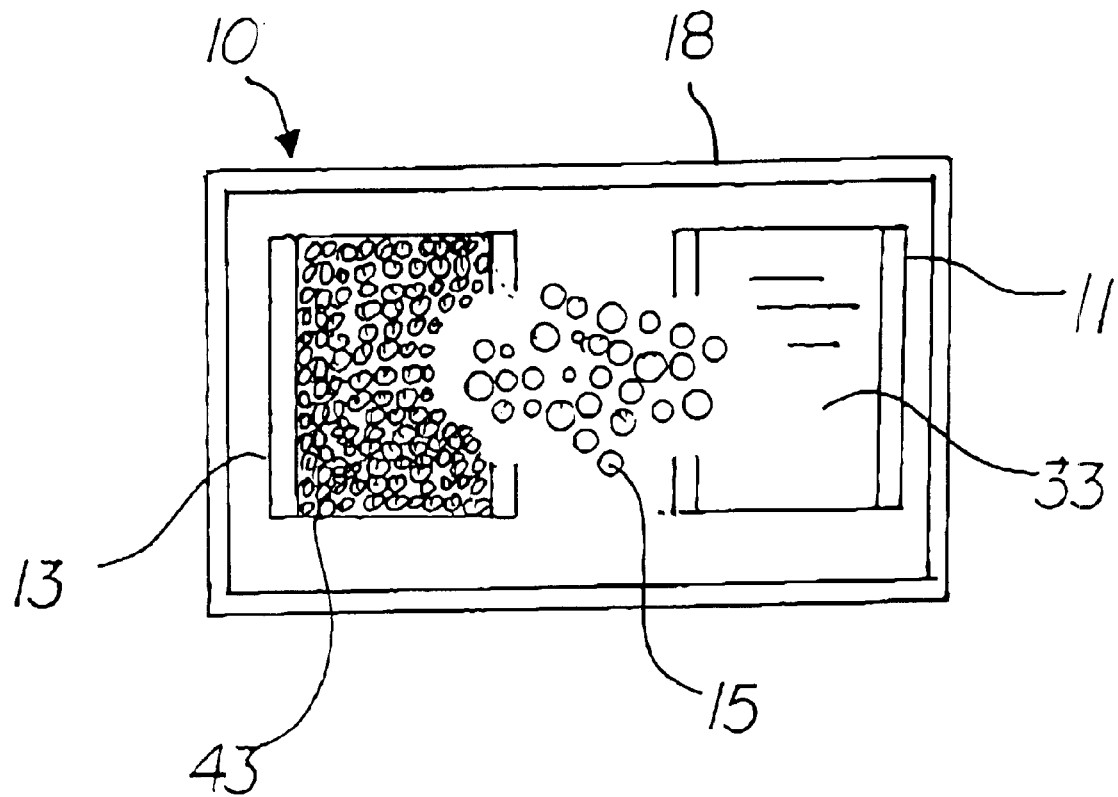
FIG. 1 is a top plan view of a thermal pack in accordance with one embodiment of the invention.
Figure 2:
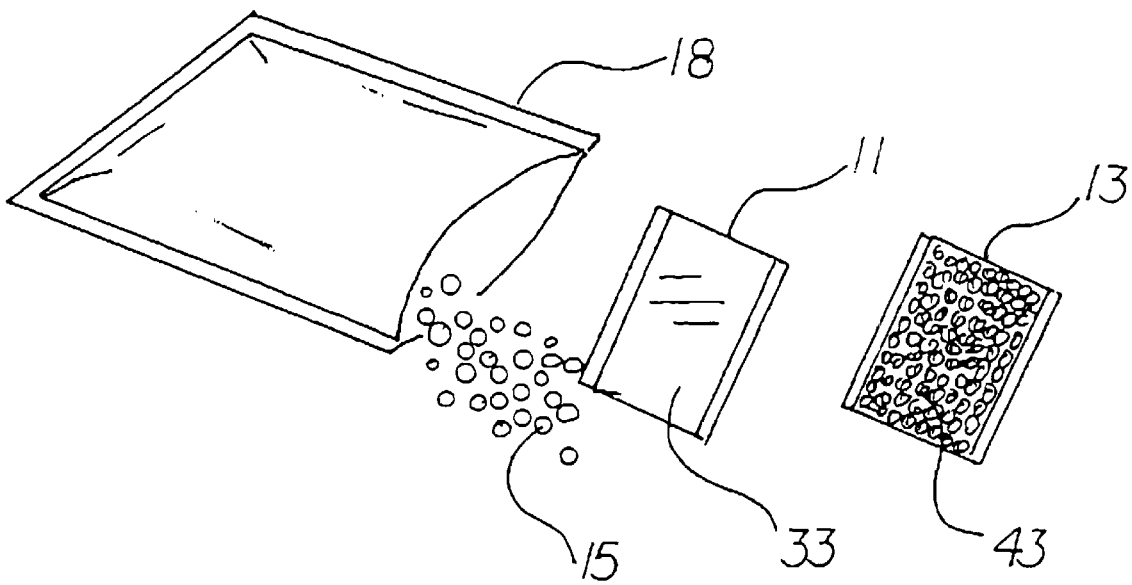
FIG. 2 is an angled perspective exploded view of the thermal pack of FIG. 1.

Referring to FIG. 1, a thermal pack 10 made in accordance with the invention includes a container 18 and a first thermally reactive chemical solute 15 disposed therein. Also disposed within the container 18 is a rupturable solvent packet 11 containing a solvent 33 therein, and a rupturable solute packet 13 containing a second thermally reactive chemical solute 43 therein. FIG. 2 illustrates the components of a thermal pack according to the invention in disassembled condition with an opened container 18.

Figure 3:
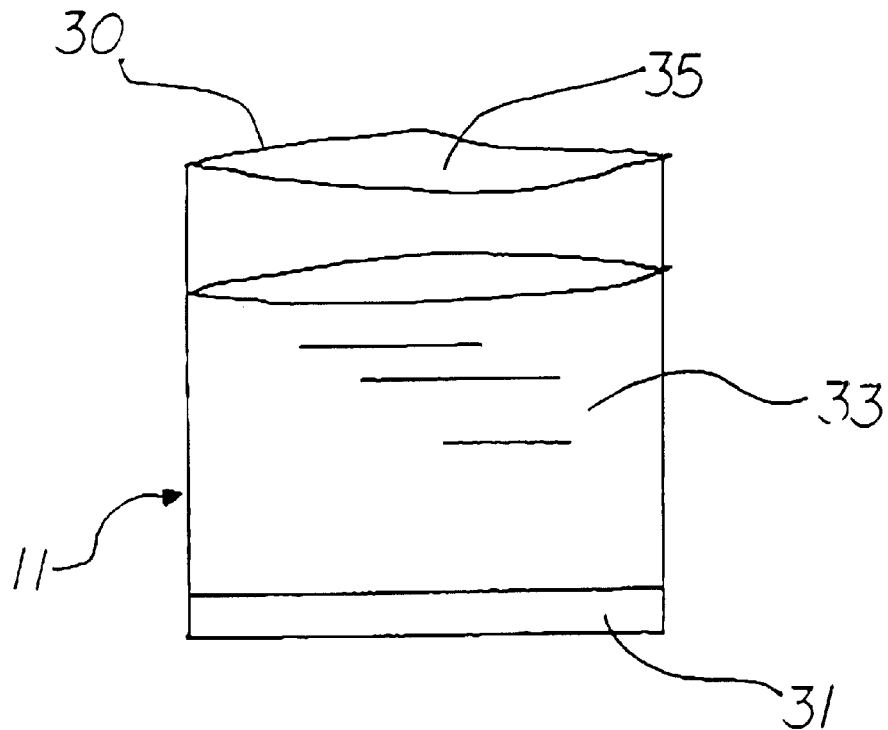
FIG. 3 is a side view of a solvent in an open sealable packet of the thermal pack of FIG. 1.

A solvent packet is illustrated in FIG. 3. The solvent packet 11 is in the general configuration of a pouch and is composed of a flexible material 30 and contains a solvent 33 therein. In the embodiment shown in FIG. 3, the solvent packet 11 has a bottom seal 31 and an opening 35 along one side. The solvent 33 is added to the packet 11 prior to sealing the opening 35. Once sealed, the solvent packet 11 encases the solvent 33 and chemically separates the solvent 33 from the other chemical ingredients in the container 18 (as seen in other Figures) until ruptured by the user.

Figure 4:
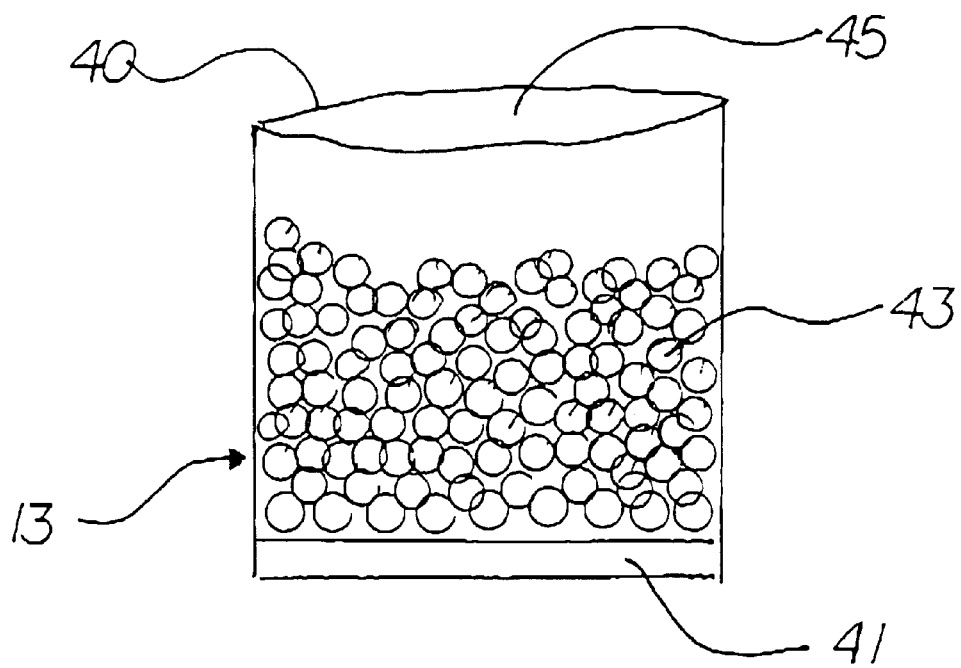
FIG. 4 is side view of a solute in an open sealable packet of the thermal pack of FIG. 1.

FIG. 4 shows a solute packet 13 having an opening 45 and seal 41, and containing a thermally reactive chemical solute 43 deposited therein. In a manner similar to the solvent packet discussed above, the solute 43 is added to the packet 13 through the opening 45 prior to sealing, thereby chemically separating the solute from the remaining ingredients in the container 18 (as seen in other Figures).

The container and packet materials can be composed of any flexible polymeric material adapted to be sealed and ruptured. Suitable polymeric materials include, but are not limited to, polyethylene, polypropylene, polybutylene, polyvinylchloride, polyester, polyethylene terephthalate, vinylidene chloride polymers, and combinations thereof. The container and packet materials can be in the form of laminates, copolymers, and co-extruded films.

The container and packets are sealable after the depositing of the contents in the manufacturing stage. Any conventional sealing technique known in the art can be used to seal or fuse the open end of the packet, such as heat sealing, ultrasonic or radio frequency (RF) welding or adhesive techniques.

The solvent and solute packets housed within the container are both rupturable and sealable. The rupturable packets are adapted to be ruptured by physical forces exerted upon the pack by the user at the time of use. In one embodiment, a portion of the packet can be scored or perforated to facilitate rupturing of the packet to release the contents. Rupturing of the solvent packet releases the solvent thereby permitting the solvent to combine with the first solute in the container and initiate the thermal reaction. Rupturing the solute packet permits the second solute to combine with the first solute and solvent thereby furthering the thermal reaction after the first solute has reacted.

The temperature produced by thermal packs of the invention are within a therapeutically useful temperature range. In the case of cold packs, the temperature is preferably greater than about 10° F. (−12° C.). In the case of hot packs, the temperature is preferably greater than about 104° F. (40° C.). Even more preferred for hot packs is a temperature ranging from about 104° to about 114° F. (about 40° C. to about 46° C.). In order to control the maximum temperature of hot packs, a latent heat absorber can be added to the solute mixture to prevent the creation of excessive heat resulting from the exothermic reaction. Heat absorbers which can be used include any conventional material which can absorb heat suitable for thermal pack applications.

The life of the thermal pack is conventionally defined according to the time the pack remains at a certain temperature once activated, and is generally without reference to the extreme temperature the thermal pack reaches upon activation. The temperature can be measured at the surface of the thermal pack or within the interior of the pack.

In the case of a cold pack, the life of the cold pack is conventionally defined as the time the pack remains below 50° F (10° C.) once it is activated. A cold pack exhibiting an extended life is one which remains below 50° F. (10° C.) for a longer period of time than a cold pack which uses either the first endotherm-producing chemical or second endotherm-producing chemical individually such that the total weight of endotherm-producing chemicals in both of the cold packs is about the same. It is also desirable that the minimum temperature reached by the cold pack once activated at room temperature, be no less than about 10° F. (−12° C.). Room temperature will range from about 65° F. to about 75° F. (about 18° C. to about 24° C.).

The solvent used in the thermal packs of the invention can be any solvent adapted to dissolve and react with endothermic or exothermic compounds to result in a thermal reaction within a therapeutically useful temperature range. The preferred solvent for use in cold packs according to the invention is water.

With respect to cold packs, the endotherm-producing chemicals or solutes are those which react with the solvent, or water, to produce a reduced temperature. Endotherm-producing chemicals include, but are not limited to, ammonium nitrate, ammonium sulfamate, ammonium nitrite, ammonium iodide, ammonium bromide, sodium chloride, sodium nitrate, sodium nitrite, sodium carbonate, sodium bicarbonate, potassium nitrate, potassium nitrite, urea, methylurea, potassium chloride, $SnCl_2$—$2H_2O$, $Co(NH_2)_2$, $CoCl_2$—$6H_2O$, $Ni(NO_3)_2$—$6H_2O$, and combinations thereof. Preferably, the combination of the solute with the solvent (e.g., water) has a positive enthalpy of solution and produces a reduced temperature greater than about 10° F. (−12° C.) when dissolved in room temperature solvent.

A preferred cold pack of the invention contains ammonium nitrate as the first endotherm-producing chemical and urea as the second endotherm-producing chemical. Ammonium nitrate and urea can be interchanged as the second endotherm-producing chemical and first endotherm-producing chemical respectively without adversely affecting the desired properties of the pack when both are simultaneously used.

In the case of hot packs according to the invention, the exotherm-producing chemicals or solutes are those which react with the solvent, or water, to produce an elevated temperature. Exotherm-producing chemicals include, but are not limited to, calcium chloride, calcium bromide, sodium acetate, potassium permanganate, calcium klesserite, magnesium sulfate, aluminum chloride, magnesium bromide, magnesium chloride, manganese chloride, manganese nitrate, nickel chloride, zinc chloride, ferric chloride, and combinations thereof. Preferably, the combination of the solutes with the solvent (e.g., water) has a negative enthalpy of solution and produces an elevated temperature greater than about 104° F. (40° C.) when dissolved in room temperature solvent.

The endotherm-producing chemicals and exotherm-producing chemicals are selected according to their ability to react with the solvent and the other thermally reactive solute to result in a thermal pack which has an extended life. Generally, the combination of the endotherm-producing chemicals with one another, and likewise the exotherm-producing chemicals with one another, is a solute-solute mixture. Such mixtures can possess a surprising synergy that produces for an extended time a useful temperature when compared to the results when either thermally reactive solute is used separately.

The amount and proportions of each of the solutes and solvent relative to one another can vary provided the amount of thermally reactive solutes are present in an amount so that the solvent remains unsaturated following combination with at least the first solute, and provided that the desired reaction between the solvent(s) and solutes is obtained. When three or more solutes are used, the amount of solute present in the pack is an amount in which the solvent remains unsaturated following combination with the first and second solutes, and so on. Factors which affect the amount and proportion of each ingredient include, but are not limited to, concentration, desired temperature, desired rate and duration of thermal reaction, the structure of the thermal pack, and the like.

Thermal packs according to the invention can be made using conventional and known manufacturing equipment and methods in the art. Apparatuses and techniques similar to those described in Stanley, Jr. U.S. Pat. No. 3,892,060 and Francis, Jr. U.S. Pat. No. 4,856,651 can be adapted to produce the desired structure and configuration of thermal packs of the invention. For example, each of the container and rupturable packet components can be manufactured by initially sealing the perimeters of two opposing sheets of flexible material together in opposition to one another. Alternatively, the container and packets can be prepared by a manufacturing technique by initially folding a single sheet of flexible material along one side to form a double sheet arrangement and subsequently sealing along the three unattached sides to form the container or packet. In yet another alternative technique, a tube composed of flexible material can be cut at two locations and subsequently sealed thereby forming an enclosed container or packet. The contents of the container or packet are deposited therein prior to sealing. The number of packets, order of deposition of contents, sealing locations and sealing order of each component, and the like, can be selected to produce the desired thermal pack structure and configuration.

A variety of activation techniques can be applied to the thermal packs of the invention by the different component selection and rupturing sequences. Activation of the thermal packs can be performed by simultaneous rupture of both the solvent packet and the solute packet such that the solvent and second thermally reactive solute simultaneously combine with the first thermally reactive solute to produce the thermal effect. Alternatively, the solvent packet can be ruptured alone thereby initially combining the solvent with the first thermally reactive solute and, subsequently, the solute packet can be ruptured so that the second thermally reactive solute can further react with the solvent. Each of the embodiments of the invention provide various options with respect to the activation of the thermal pack by virtue of the pack structure. In addition to the selection of chemicals used in the pack, theduration of thermal affect can be further extended by sequentially rupturing the solute packets, solvent packets or a combination thereof, depending upon the particular pack structure. The invention affords the user more control over the duration and timing of the thermal effect.

Once activated, the thermal pack is then applied to the body to provide the thermal treatment. The step of applying the thermal pack to the body can occur at any point after the initiation of the thermal reaction. Then various rupturing sequences which are possible likewise afford to the user various options with regard to points in time of applying the pack.

Figure 5:
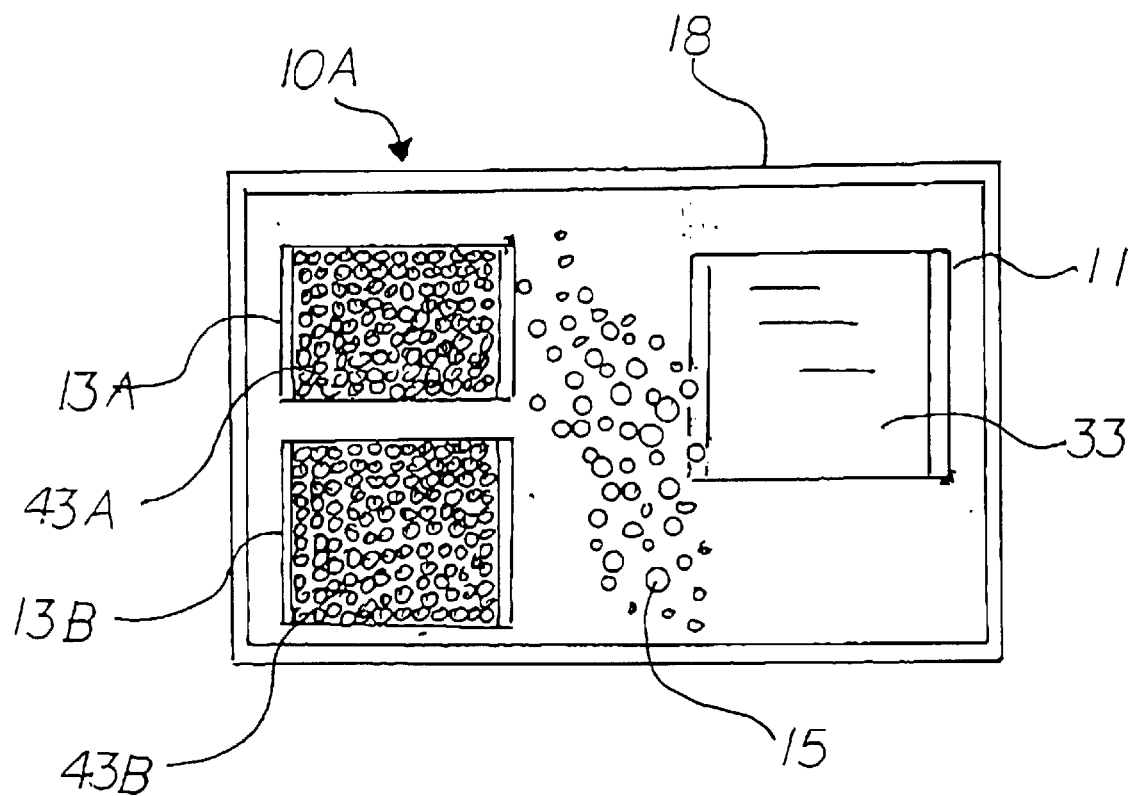
FIG. 5 is a top plan view of a thermal pack having one solvent packet and two solute packets in addition to a thermally reactive solute contained in the thermal pack according to one embodiment of the invention.

Various combinations of solvents and solvent packets, solutes and solute packets, and containers can be used to afford both chemical and structural means to extend the duration of thermal effect and enable the user better control over the pack. Likewise, the number of each of these components within a single thermal pack unit can vary as well. One embodiment is depicted in FIG. 5, wherein the thermal pack 10A includes a sealed container 18, a rupturable solvent pack 11 containing a solvent 33 therein, a first thermally reactive solute 15 disposed within the container, and further includes a first solute packet 13A containing a second thermally reactive solute 43A and second solute packet 13B with a third solute 43B therein.

Figure 6:
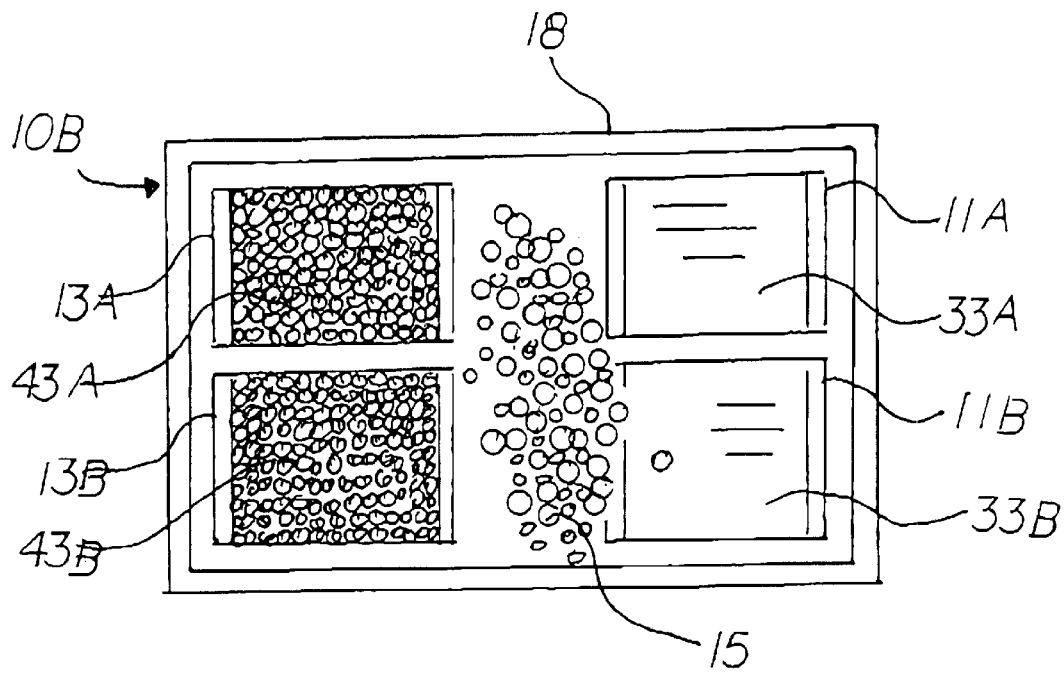
FIG. 6 is a top plan view of a thermal pack having two separate solvent packs and two solute packets in addition to a thermally reactive solute contained in the thermal pack in accordance with one embodiment of the invention.

FIG. 6 illustrates another embodiment of the thermal pack 10B according to the invention which includes a first rupturable solvent packet 11A containing a first solvent therein 33A and a second rupturable solvent packet 11B containing a second solvent therein 33B. First and second rupturable solute packets, 13A and 13B respectively containing second solute 43A and third solute 43B respectively, are also within single container 18. The first and second solvents can be identical or different, provided the solutes to be combined therewith can be dissolved thereby. In use, the rupturing sequence and timing can be varied by the user to produce the desired combination of effect and duration.

Figure 7:
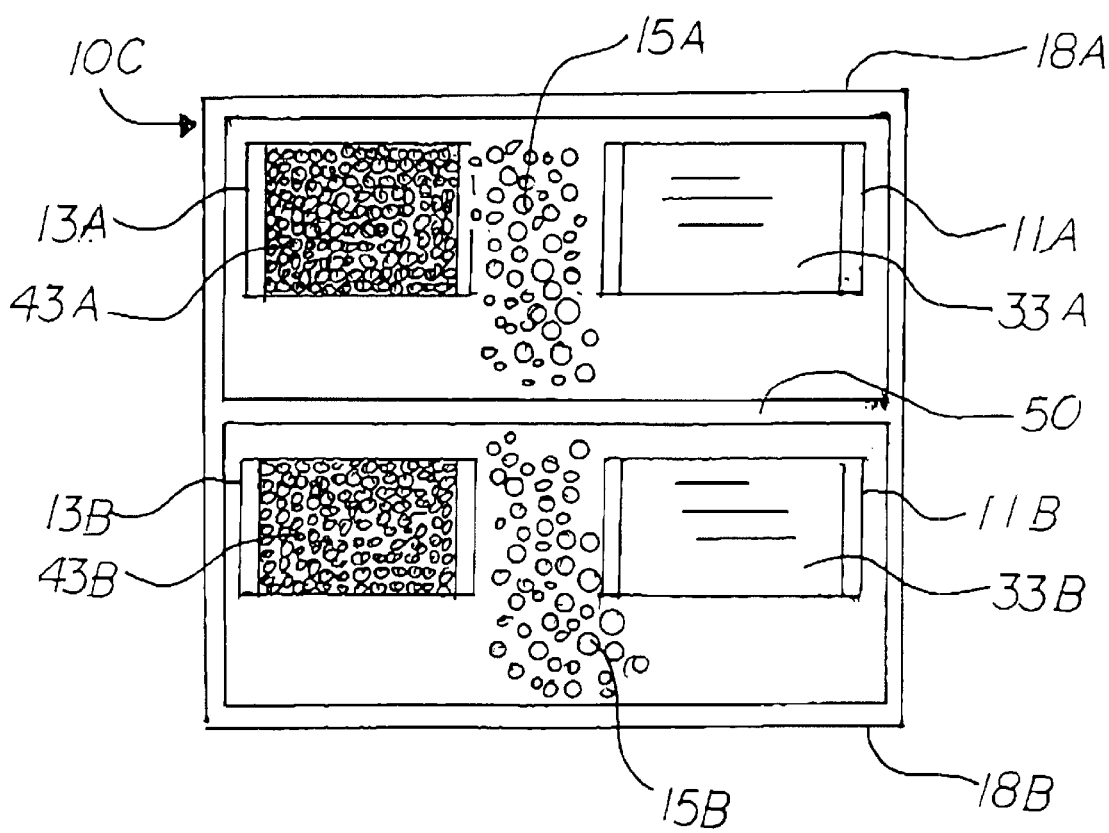
FIG. 7 is a top plan view of a thermal pack having first and second separate containers in accordance with one embodiment of the invention.

Referring now to FIG. 7, another embodiment of the thermal pack of the invention is illustrated, wherein a single thermal pack 10C which includes first and second separated containers 18A and 18B respectively, each container having a solvent packet (11A and 11B), a first rupturable solute packet 13A containing a first thermally reactive solute 43A therein, and a second rupturable solute packet 13B containing a second thermally reactive solute 43B therein. The containers can be separated by a seal 50 therebetween to prevent admixture of the respective contents.

In each of the above embodiments, each of the solvent(s) and solutes are chemically separated until use, and at least two of the solutes are different from one another.

The effectiveness of different thermal pack formulations can be laboratory tested by placing the components in a beaker or other suitable container and measuring the generated temperatures under mixing. The following examples illustrate the advantageous properties of the thermal pack according to the invention.

EXAMPLE 1

Ammonium nitrate, urea and water were mixed in a beaker. The temperature of the mixture was measured and recorded from the start of mixing through the time it took for the mixture to return to 50° F. (10° C.). The lowest temperature reached was also recorded. Varying amounts of ammonium nitrate and urea were also tested. The results of these measurements is presented in Table 1 below:

TABLE 1

| Time to Reach 50° F. | Lowest Temperature Reached, ° F. | Ammonium Nitrate (grams) | Urea (grams) | Water (grams) |
| --- | --- | --- | --- | --- |
| 25.4 | 19.2 | 67 | 40 | 100 |
| 31.8 | 16.9 | 67 | 50 | 100 |
| 32.0 | 15.7 | 67 | 60 | 100 |
| 29.8 | 15.5 | 67 | 70 | 100 |
| 41.8 | 13.2 | 67 | 80 | 100 |

As a comparison, ammonium nitrate and water were mixed in a beaker. The temperature of the mixture was measured, and the time for the mixture to return to 50° F. (10° C.) from the start of mixing, were recorded. The lowest temperature reached was also recorded. Measurements were made of different solutions wherein the amount of ammonium nitrate was varied. The amounts of ammonium nitrate and water given in Table 2 are conventional quantities used in cold packs of the prior art. The results of these measurements are presented in Table 2 below:

TABLE 2

| Time to Reach 50° F. | Lowest Temperature Reached, ° F. | Ammonium Nitrate (grams) | Urea (grams) | Water (grams) |
| --- | --- | --- | --- | --- |
| 20.0 | 28.0 | 67 | 0 | 100 |
| 35.0 | 21.7 | 150 | 0 | 100 |
| 26.2 | 26.3 | 100 | 0 | 150 |
| 18.3 | 30.4 | 75 | 0 | 112.5 |
| 21.2 | 34.0 | 0 | 67 | 100 |

A comparison of the results in Table 1 with Table 2 demonstrates that a cold pack of the invention provides an extended life at a reduced temperature. The results also demonstrate that a cold pack of the instant invention does not first establish an unusable lowest temperature. The results further demonstrate that an extended life at a reduced temperature is achieved using conventional amounts of endotherm-producing chemicals.

EXAMPLE 2

Further tests were performed using a circulatory water pad (hereinafter referred to as the "pad"). The pad has an interior pocket into which an extended life cold pack, including endotherm-producing chemicals can be placed. The interior pocket defines an area for an applied test sample consisting of the cold pack. For these tests, the pad was wrapped two times around a rolled towel. The towel was rolled to simulate a human arm. The temperature of circulating fluid was set at 99° F. Thermocouple probes were placed on the pad and within an area of an applied test sample. Temperatures of each applied test sample were recorded for a minimum of 40 minutes. Every few minutes during the temperature recording, the applied test sample was slightly agitated, but not removed from the area. This agitation was to stimulate a mild level of agitation that occurs in normal use.

In this example, the performances of cold packs made according to the invention were compared to the performance of a control cold pack. In the control cold pack, the pad was filled with 218 grams of water and 145 grams of ammonium nitrate. The cold packs of the invention were prepared by adding different weights of urea to the pad containing 218 grams of water and 145 grams of ammonium nitrate. Table 3, produced below, identifies the compositions tested and the results of this testing. The time shown in Table 3 is the elapsed time measured from the activation of the endotherm-producing chemicals. The ambient air temperature in which the tests were conducted was nominally 75° F. (23° C.).

TABLE 3

| Water (grams) | Ammonium Nitrate (grams) | Urea (grams) | Time (minutes) | | | | | | | | |
| --- | --- | --- | --- | --- | --- | --- | --- | --- | --- | --- | --- |
| | | | 1 | 5 | 10 | 15 | 25 | 40 | 60 | 90 | 120 |
| | | | Temperature (° F.) | | | | | | | | |
| 218 | 145 | 0 | 31.1 | 30.0 | 33.8 | 38.3 | 45.4 | 52.2 | 48.7 | | |
| 218 | 145 | 80 | 30.0 | 31.4 | 29.3 | 30.1 | 34.2 | 41.4 | | | |
| 218 | 145 | 145 | 36.5 | 35.2 | 33.7 | 34.2 | 37.1 | 41.4 | 46.7 | 44.0 | 53.9 |

While the results presented in Table 1 and Table 2 demonstrate the efficacy of the present invention, the results presented in Table 3 more closely approximate the results expected from actual use of the cold pack made in accordance with the present invention. For example, the use of 145 grams of urea, together with 145 grams of ammonium nitrate and 218 grams of water, effectively triples the life of the cold pack as compared to the case where urea is not used. Additionally, an initial temperature of the pack, at 1 minute and at 5 minutes, is effectively unchanged by the incorporation of urea. Thus, it can also be seen that the provision of an extended life cold pack according to the principles of the present invention is not simply a mater of increasing the total amount of endotherm-producing chemicals used.

One skilled in the art of cold packs would expect that increasing the amount of endotherm-producing chemicals would result in an increase in the life of the cold pack. Such a relationship is illustrated for the conventional composition of Table 2. Unexpectedly, no such concentration dependency is evident in the present invention, as illustrated by the results of Table 1 and 3. Furthermore, the initial temperature is independent of the amount of second endotherm-producing chemical used.

EXAMPLE 3

In order to further assess the effect of combining a first erndotherm-producing chemical and a second endotherm-producing chemical, the heat absorbed by the water in a cold pack was calculated. In this example, a cold pack made according to the invention was compared to a conventional cold pack. The heat absorbed is calculated using the following formula:

Heat Absorbed (Joules)=4.18×$\Delta T$×W,

Wherein $\Delta T$=the initial temperature minus the final temperature (° C.); and W=the weight of water plus the weight of a calorimeter containing the water.

In performing the experiments for Example 3, water, contained within a sealed pouch, was first placed into a flask and heated to about 155° F. (68° C.). The heated pouch was then placed into a standard laboratory calorimeter equipped with a temperature data log. The calorimeter was positioned on a standard laboratory shaker. The orbital shaker was set to operate at 120 revolutions per minute. The temperature data log was activated and the orbital shaker was activated. The temperature data log and the orbital shaker were in operation throughout the remainder of the experiment. Typically, the temperature in the calorimeter reached a equilibrium value within about 5 minutes of the placement of the heated pouch. This equilibrium temperature was recorded as the initial temperature. Next, ammonium nitrate and urea were added to the calorimeter, the pouch was ruptured, and the water, urea and ammonium nitrate were allowed to mix. The temperature recorded by the data log was presented as a curve in a plot of temperature as a function of time. Due to the endothermic reaction of the mixture the temperature of the mixture decreased, reached a plateau, and then began to increase. The plateau temperature reached by the mixture was measured by the data log and recorded as the final temperature. The results of Example 3 are presented in Table 4 below:

TABLE 4

| Experiment | 1 | 2 | 3 | 4 |
|---|---|---|---|---|
| Total mixture weight, grams | 555.5 | 538.3 | 539.6 | 530.4 |
| Weight of water, grams | 333.3 | 323.0 | 323.8 | 207.4 |
| Weight of ammonium nitrate, grams | 222.2 | 215.3 | 215.8 | 146.1 |
| Weight of urea, grams | 0 | 0 | 0 | 176.9 |
| Weight of water plus the calorimeter | 926.5 | 993.4 | 865.4 | 1008.6 |
| Initial Temperature, ° F. | 153.0 | 152.5 | 150.8 | 151.0 |
| Final Temperature, ° F. | 135.0 | 136.0 | 132.8 | 129.0 |
| $\Delta T$, ° F. | 18.0 | 16.5 | 18.0 | 22.0 |
| $\Delta T$, ° C. | 10.0 | 9.2 | 10.0 | 12.2 |
| Heat Absorbed, Joules | 38727.70 | 38063.78 | 36173.72 | 51528.25 |
| Heat Absorbed per gram of mixture, Joules | 69.72 | 70.71 | 67.04 | 97.15 |

The results of Example 3 presented in Table 4 above illustrate the significantly greater heat absorbing capacity of a cold pack made according to the invention. When compared to conventional cold pack compositions, the cold pack of the present invention absorbs at least 24.8% more heat.

Industrial Applicability:

The medical industry and consumers are constantly in search of improved products. The invention provides the user with the combined benefits of extended duration thermal treatment and user control as compared to conventional thermal packs. Furthermore, conventional manufacturing equipment and techniques can be used to manufacture the improved thermal packs of the invention.

The complete disclosures of all patents, patent applications, and publications are incorporated herein by reference as if each were individually incorporated by reference. The invention has been described with reference to various specific and preferred embodiments and techniques. However, it should be understood that many variations and modifications can be made without departing from either the spirit or scope of the invention.

What is claimed is:

1. A thermal pack adapted to extend the duration of thermal effect comprising:

a container sealed to the atmosphere;

a first thermally reactive chemical solute disposed within said container;

a rupturable solvent packet disposed within said container;

a solvent disposed within said solvent packet;

a rupturable solute packet disposed within said container;

a second thermally reactive chemical solute disposed within said solute packet;

wherein each of the solvent, first and second thermally reactive solutes are chemically separated and wherein the first thermally reactive solute is different from the second thermally reactive solute.

2. A thermal pack according to claim 1 wherein the first thermally reactive solute is present in an amount in which the solvent is unsaturated following the combination therewith.

3. A thermal pack according to claim 1 which is a cold pack.

4. A thermal pack according to claim 3 wherein the first thermally reactive solute is an endotherm-producing chemical and the second thermally reactive solute is an endotherm-producing chemical.

5. A thermal pack according to claim 4 wherein each of the endotherm-producing chemicals is selected from the group consisting of ammonium nitrate, ammonium sulfamate, ammonium nitrite, ammonium iodide, ammonium bromide, sodium chloride, sodium nitrate, sodium nitrite, sodium carbonate, sodium bicarbonate, potassium nitrate, potassium nitrite, urea, methylurea,, $SnCl_2$—$2H_2O$, $Co(NH_2)_2$, $CoCl_2$—$6H_2O$, $Ni(NO_3)_2$—$6H_2O$, and combinations thereof.

6. A thermal pack according to claim 4 wherein the combination of one or more of the endotherm-producing chemicals with the solvent produces a reduced temperature of greater than about 10° F. (−12° C.).

7. The thermal pack of claim 1 wherein the solvent is a solvent adapted to dissolve and react with thermally reactive solutes to result in a thermal reaction within a therapeutically useful temperature range.

8. The thermal pack of claim 7 wherein the solvent is water.

9. A thermal pack according to claim 1 which is a hot pack.

10. A thermal pack according to claim 9 wherein the first thermally reactive solute is an exotherm-producing chemical and the second thermally reactive solute is an exotherm-producing chemical.

11. A thermal pack according to claim 10 wherein each of the exotherm-producing chemicals provides a negative heat of solution and is selected from the group consisting of calcium chloride, calcium bromide, sodium acetate, potassium permanganate, calcium klesserite, magnesium sulfate, aluminum chloride, magnesium bromide, magnesium chloride, manganese chloride, manganese nitrate, nickel chloride, zinc chloride, ferric chloride, and combinations thereof.

12. A thermal pack according to claim 10 wherein the combination of one or more of the exotherm-producing chemicals with the solvent produces an elevated temperature of greater than about 104° F. (40° C.).

13. A thermal pack adapted to extend the duration of thermal effect comprising:
a container sealed to the atmosphere;
a first thermally reactive chemical solute disposed within said container;
a rupturable solvent packet disposed within said container;
a solvent disposed within said solvent packet;
a first rupturable solute packet disposed within said container;
a second thermally reactive chemical solute disposed within said first rupturable solute packet;
a second rupturable solute packet disposed within said container;
a third thermally reactive chemical solute disposed within said second rupturable solute packet;
wherein each of the solvent, first, second and third thermally reactive solutes are chemically separated and wherein at least two of the first, second and third thermally reactive solutes are different from each other.

14. A thermal pack according to claim 13 wherein the first and second thermally reactive solutes are present in an amount in which the solvent is unsaturated following combination therewith.

15. A thermal pack according to claim 13 which is a cold pack.

16. A thermal pack according to claim 13 wherein the first thermally reactive solute is an endotherm-producing chemical, the second thermally reactive solute is an endotherm-producing chemical, and the third thermally reactive solute is an endotherm-producing chemical.

17. A thermal pack according to claim 16 wherein each of the endotherm-producing chemicals is selected from the group consisting of ammonium nitrate, ammonium sulfamate, ammonium nitrite, ammonium iodide, ammonium bromide, sodium chloride, sodium nitrate, sodium nitrite, sodium carbonate, sodium bicarbonate, potassium nitrate, potassium nitrite, urea, methylurea, $SnCl_2$—$2H_2O$, $Co(NH_2)_2$, $CoCl_2$—$6H_2O$, $Ni(NO_3)_2$—$6H_2O$, and combinations thereof.

18. A thermal pack according to claim 16 wherein the combination of one or more of the endotherm-producing chemicals with the solvent produces a reduced temperature of greater than about 10° F. (−12° C.).

19. The thermal pack of claim 13 wherein the solvent is a solvent adapted to dissolve and react with the thermally reactive solutes to result in a thermal reaction within a therapeutically useful temperature range.

20. The thermal pack of claim 19 wherein the solvent is water.

21. A thermal pack according to claim 13 which is a hot pack.

22. A thermal pack according to claim 21 wherein the first thermally reactive solute is an exotherm-producing chemical, the second thermally reactive solute is an exotherm-producing chemical, and the third thermally reactive solute is an endotherm-producing chemical.

23. A thermal pack according to claim 22 wherein each of the exotherm-producing chemicals is selected from the group consisting of calcium chloride, calcium bromide, sodium acetate, potassium permanganate, calcium klesserite, magnesium sulfate, aluminum chloride, magnesium bromide, magnesium chloride, manganese chloride, manganese nitrate, nickel chloride, zinc chloride, ferric chloride, and combinations thereof.

24. A thermal pack according to claim 22 wherein the combination of one or more of the exotherm-producing chemicals with the solvent produces an elevated temperature of greater than about 104° F. (40° C.).

25. A thermal pack adapted to extend the duration of thermal effect comprising:
a container sealed to the atmosphere;
a first thermally reactive chemical solute disposed within said container;
a first rupturable solvent packet disposed within said container;
a first solvent disposed within said first solvent packet;
a second rupturable solvent packet disposed within said container;
a second solvent disposed within said second solvent packet;
a first rupturable solute packet disposed within said container;

a second thermally reactive chemical solute disposed within said first solute packet;

a second rupturable solute packet disposed within said container;

a third chemically reactive solute disposed within said second rupturable solute packet;

wherein each of the first and second solvents, first, second and third thermally reactive solutes are chemically separated, and wherein at least two of the first, second and third thermally reactive solutes are different from each other.

26. A thermal pack according to claim 25 wherein the first thermally reactive solute is present in an amount in which the first solvent is unsaturated following combination therewith.

27. A thermal pack according to claim 25 which is a cold pack.

28. A thermal pack according to claim 27 wherein the first thermally reactive solute is an endotherm-producing chemical, the second thermally reactive solute is an endotherm-producing chemical, and the third thermally reactive solute is an endotherm-producing chemical.

29. A thermal pack according to claim 28 wherein each of the endotherm-producing chemicals is selected from the group consisting of ammonium nitrate, ammonium sulfamate, ammonium nitrite, ammonium iodide, ammonium bromide, sodium chloride, sodium nitrate, sodium nitrite, sodium carbonate, sodium bicarbonate, potassium nitrate, potassium nitrite, urea, methylurea, $SnCl_2—2H_2O$, $Co(NH_2)_2$, $CoCl_2—6H_2O$, $Ni(NO_3)_2—6H_2O$, and combinations thereof.

30. A thermal pack according to claim 28 wherein the combination of one or more of the endotherm-producing chemicals with the solvent produces a reduced temperature of greater than about 10° F. (−12° C.).

31. The thermal pack of claim 25 wherein the solvent is a solvent adapted to dissolve and react with the thermally reactive solutes to result in a thermal reaction within a therapeutically useful temperature range.

32. The thermal pack of claim 31 wherein the solvent is water.

33. A thermal pack according to claim 25 which is a hot pack.

34. A thermal pack according to claim 33 wherein the first thermally reactive solute is an exotherm-producing chemical, the second thermally reactive solute is an exotherm-producing chemical, and the third thermally reactive solute is an exotherm-producing chemical.

35. A thermal pack according to claim 34 wherein each of the exotherm-producing chemicals is selected from the group consisting of calcium chloride, calcium bromide, sodium acetate, potassium permanganate, calcium klesserite, magnesium sulfate, aluminum chloride, magnesium bromide, magnesium chloride, manganese chloride, manganese nitrate, nickel chloride, zinc chloride, ferric chloride, and combinations thereof.

36. A thermal pack according to claim 34 wherein the combination of one or more of the exotherm-producing chemicals with the solvent produces an elevated temperature of greater than about 104° F. (40° C.).

37. The thermal pack of claim 25 wherein the solvent is a solvent adapted to dissolve and react with the thermally reactive solutes to result in a thermal reaction within a therapeutically useful temperature range.

38. The thermal pack of claim 37 wherein the solvent is water.

39. A thermal pack adapted to extent the duration of thermal effect having first and second containers each sealed to the atmosphere and from the other, each of said first and second containers comprising:

a first thermally reactive chemical solute disposed within said container;

a rupturable solvent packet disposed within said container;

a solvent disposed within said solvent packet;

a rupturable solute packet disposed within said container;

a second thermally reactive chemical solute disposed within said rupturable solute packet;

wherein each of the solvent, first and second thermally reactive solutes are chemically separated and wherein the first thermally reactive solute is different from the second thermally reactive solute.

40. The thermal pack of claim 39, wherein the first thermally reactive solute is present in a concentration and quantity in which the solvent is unsaturated following combination therewith.

41. The thermal pack of claim 39 which is a cold pack.

42. The thermal pack of claim 41 wherein the first thermally reactive solute is an endotherm-producing chemical and the second thermally reactive solute is an endotherm-producing chemical.

43. The thermal pack of claim 42 wherein each of the endotherm-producing chemicals is selected from the group consisting of ammonium nitrate, ammonium sulfamate, ammonium nitrite, ammonium iodide, ammonium bromide, sodium chloride, sodium nitrate, sodium nitrite, sodium carbonate, sodium bicarbonate, potassium nitrate, potassium nitrite, urea, methylurea, $SnCl_2—2H_2O$, $Co(NH_2)_2$, $CoCl_2—6H_2O$, $Ni(NO_3)_2—6H_2O$, and combinations thereof.

44. The thermal pack of claim 42 wherein the combination of one or more of the endotherm-producing chemicals with the solvent produces a reduced temperature of greater than about 10° F. (−12° C.).

45. The thermal pack of claim 39 wherein the solvent is a solvent adapted to dissolve and react with the thermally reactive solutes to result in a thermal reaction within a therapeutically useful temperature range.

46. The thermal pack of claim 45 wherein the solvent is water.

47. The thermal pack of claim 39 which is a hot pack.

48. The thermal pack of claim 47 wherein the first thermally reactive solute is an exotherm-producing chemical and the second thermally reactive solute is an exotherm-producing chemical.

49. The thermal pack of claim 48 wherein each of the exotherm-producing chemicals is selected from the group consisting of calcium chloride, calcium bromide, sodium acetate, potassium permanganate, calcium klesserite, magnesium sulfate, aluminum chloride, magnesium bromide, magnesium chloride, manganese chloride, manganese nitrate, nickel chloride, zinc chloride, ferric chloride, and combinations thereof.

50. The thermal pack of claim 48 wherein the combination of one or more of the exotherm-producing chemicals with the solvent produces an elevated temperature of greater than about 104° F. (40° C.).

51. A method of applying thermal treatment to a body comprising:

selecting a thermal pack adapted to extend the duration of thermal effect comprising:

a container sealed to the atmosphere;

a first thermally reactive chemical solute disposed within said container;

a rupturable solvent packet disposed within said container;

a solvent disposed within said solvent packet;

a rupturable solute packet disposed within said container;

a second thermally reactive chemical solute disposed within said solute packet;

wherein each of the solvent, first and second thermally reactive solutes are chemically separated and wherein the first thermally reactive solute is different from the second thermally reactive solute;

rupturing solvent packet so as to combine with first solute;

rupturing the solute packet thereby combining the second solute with the solvent; and applying the thermal pack to the body.

52. The method of claim 51 wherein said thermal treatment is cold therapy.

53. The method of claim 51 wherein said thermal treatment is heat therapy.

54. A method of applying thermal treatment to a body comprising:

selecting a thermal pack adapted to extend the duration of thermal effect comprising:

a container sealed to the atmosphere;

a first thermally reactive chemical solute disposed within said container;

a rupturable solvent packet disposed within said container;

a solvent disposed within said solvent packet;

a first rupturable solute packet disposed within said container;

a second thermally reactive chemical solute disposed within said first rupturable solute packet;

a second rupturable solute packet disposed within said container;

a third thermally reactive chemical solute disposed within said second rupturable solute packet;

wherein each of the solvent, first, second and third thermally reactive solutes are chemically separated and wherein at least two of the first, second and third thermally reactive solutes are different from each other;

rupturing solvent packet so as to combine with first solute;

rupturing the first solute packet thereby combining the second solute with the solvent;

rupturing the second solute packet thereby combining a third solute with the solvent; and applying the thermal pack to the body.

55. The method of claim 54 wherein said thermal treatment is cold therapy.

56. The method of claim 54 wherein said thermal treatment is heat therapy.

57. A method of applying thermal treatment to a body comprising:

selecting a thermal pack adapted to extend the duration of thermal effect comprising:

a container sealed to the atmosphere;

a first thermally reactive chemical solute disposed within said container;

a first rupturable solvent packet disposed within said container;

a first solvent disposed within said first solvent packet;

a second rupturable solvent packet disposed within said container;

a second solvent disposed within said second solvent packet;

a first rupturable solute packet disposed within said container;

a second thermally reactive chemical solute disposed within said first solute packet;

a second rupturable solute packet disposed within said container;

a third chemically reactive solute disposed within said second rupturable solute packet;

wherein each of the first and second solvents, first, second and third thermally reactive solutes are chemically separated, and wherein at least two of the first, second and third thermally reactive solutes are different from each other;

rupturing the first solvent packet so as to combine with first solute;

rupturing the first solute packet thereby combining the second solute with the first solvent;

rupturing the second solvent packet thereby combining the second solvent with the first and second solutes;

rupturing the second solute packet thereby combining a third solute with the first and second solvent; and applying the thermal pack to the body.

58. The method of claim 57 wherein said thermal treatment is cold therapy.

59. The method of claim 57 wherein said thermal treatment is heat therapy.

60. A method of applying thermal treatment to a body comprising:

selecting a thermal pack adapted to extend the duration of thermal effect having first and second containers each sealed to the atmosphere and from the other, each of said first and second containers comprising:

a first thermally reactive chemical solute disposed within said container;

a rupturable solvent packet disposed within said container;

a solvent disposed within said solvent packet;

a rupturable solute packet disposed within said container;

a second thermally reactive chemical solute disposed within said rupturable solute packet;

wherein each of the solvent, first and second thermally reactive solutes are chemically separated and wherein the first thermally reactive solute is different from the second thermally reactive solute;

rupturing solvent packet in the first container so as to combine with first solute;

rupturing the solute packet in the first container thereby combining the second solute with the solvent;

applying the thermal pack to the body;

rupturing the solvent packet in the second container so as to combine with first solute;

rupturing the solute packet in the second container thereby combining the second solute with the solvent; and reapplying the thermal pack to the body.

61. The method of claim 60 wherein said thermal treatment is cold therapy.

62. The method of claim 60 wherein said thermal treatment is heat therapy.

* * * * *